(12) United States Patent
Song et al.

(10) Patent No.: US 9,435,747 B2
(45) Date of Patent: Sep. 6, 2016

(54) REFLECTANCE SPECTROSCOPY MEASURING AND SAMPLING SYSTEM AND METHOD FOR GEMSTONE TESTING

(71) Applicant: BIAOQI ELECTRONICS TECHNOLOGY CO., LTD., Guangzhou Science (CN)

(72) Inventors: Guangjun Song, Guangzhou (CN); Xiangli Zheng, Guangzhou (CN); Jianfeng Wu, Guangzhou (CN); Ling Gao, Guangzhou (CN)

(73) Assignee: Biaoqi Electronics Technology, Co., Ltd., Guangzhou (CN)

( * ) Notice: Subject to any disclaimer, the term of this patent is extended or adjusted under 35 U.S.C. 154(b) by 0 days.

(21) Appl. No.: 14/413,268

(22) PCT Filed: Jan. 16, 2013

(86) PCT No.: PCT/CN2013/070498
§ 371 (c)(1),
(2) Date: Jan. 7, 2015

(87) PCT Pub. No.: WO2014/071700
PCT Pub. Date: May 15, 2014

(65) Prior Publication Data
US 2015/0233839 A1      Aug. 20, 2015

(30) Foreign Application Priority Data
Nov. 6, 2012   (CN) .......................... 2012 1 0439044

(51) Int. Cl.
*G01N 21/00*  (2006.01)
*G01N 21/87*  (2006.01)
*G01N 21/55*  (2014.01)

(52) U.S. Cl.
CPC .............. *G01N 21/87* (2013.01); *G01N 21/55* (2013.01); *G01N 2201/061* (2013.01); *G01N 2201/065* (2013.01); *G01N 2201/0633* (2013.01); *G01N 2201/0636* (2013.01)

(58) Field of Classification Search
CPC ................. G01N 21/55; G01N 21/87; G01N 2201/065; G01J 3/0254; G01J 2001/0481
See application file for complete search history.

(56) References Cited

U.S. PATENT DOCUMENTS 3,874,799 A * 4/1975 Isaacs et al. ................... 356/402
4,395,126 A * 7/1983 Kramer ................ G01N 21/645
                                                              250/228

(Continued)

FOREIGN PATENT DOCUMENTS

CN          2052781 U        2/1990
CN          2835992 Y       11/2006

(Continued)

OTHER PUBLICATIONS

International Search Report, dated Jul. 18, 2013; 3 pages.

(Continued)

*Primary Examiner* — Kara E Geisel
*Assistant Examiner* — Maurice Smith
(74) *Attorney, Agent, or Firm* — Seyfarth Shaw LLP

(57) ABSTRACT

A reflectance spectroscopy measuring and sampling system for gemstone testing is disclosed. The system includes a first light source (1), a second light source (2), a light filtering element, an integrating sphere (S), an optical fiber (9), a spectroscopic detection module (10), an analog-digital conversion module (11) and a data processing terminal (12), wherein the integrating sphere (S) is provided with an entrance port, a sampling opening (6) and a reflected light exit port (7). A reflectance spectroscopy measuring and sampling method for gemstone testing is also disclosed. The system and the method have an excellent performance and can be widely used in the gemstone identification.

2 Claims, 4 Drawing Sheets

(56) References Cited

U.S. PATENT DOCUMENTS

| | | | |
|---|---|---|---|
| 4,482,245 A | 11/1984 | Makabe et al. | |
| 5,384,641 A * | 1/1995 | Imura | 356/446 |
| 5,580,504 A | 12/1996 | Spann et al. | |
| 6,020,959 A * | 2/2000 | Imura | 356/319 |
| 6,980,283 B1 | 12/2005 | Aggarwal | |
| 7,027,158 B2 | 4/2006 | Hendrix et al. | |
| 7,149,033 B2 * | 12/2006 | Buchsbaum | 359/618 |
| 7,206,125 B2 | 4/2007 | Wang et al. | |
| 7,375,348 B1 * | 5/2008 | Sickenberger et al. | 250/461.2 |
| 2004/0012774 A1 | 1/2004 | Lange | |
| 2008/0204705 A1 * | 8/2008 | Liu | 356/30 |
| 2010/0220310 A1 * | 9/2010 | Blodgett et al. | 356/30 |
| 2010/0309439 A1 * | 12/2010 | Bi et al. | 353/33 |
| 2012/0287432 A1 * | 11/2012 | Eckhardt et al. | 356/326 |

FOREIGN PATENT DOCUMENTS

| | | |
|---|---|---|
| CN | 201497701 A | 6/2010 |
| CN | 101858858 A | 10/2010 |
| CN | 101865838 | 10/2010 |
| CN | 101968437 | 2/2011 |
| CN | 102680103 | 9/2012 |
| JP | 5142155 | 6/1993 |
| JP | 9218159 | 8/1997 |
| JP | 9311074 A | 12/1997 |

OTHER PUBLICATIONS

Search Report & First Office Action for Priority Chinese Patent Application No. 201210439044.5, mailed on Apr. 24, 2014; 10 pages.

Second Office Action for Priority Chinese Patent Application No. 201210439044.5, mailed Jul. 25, 2014; 3 pgs.

Li et al. "Fiber Optical Spectormeter and Its Applications in On-Line Color Measurement", Guangdong Chemical Engineering, vol. 35, No. 10, pp. 112-116, Dec. 31, 2008.

\* cited by examiner

REFLECTANCE SPECTROSCOPY MEASURING AND SAMPLING SYSTEM AND METHOD FOR GEMSTONE TESTING

CROSS REFERENCE TO RELATED APPLICATIONS

This application is a national stage application of, and claims priority to, International Application No. PCT/CN2013/070498, filed Jan. 16, 2013, which claims priority to Chinese Patent Application No. CN 201210439044.5, filed Nov. 6, 2012.

FIELD

The present disclosure relates generally to a system and method for gemstone identification, and more particularly, to a reflectance spectroscopy measuring and sampling system and method for gemstone testing.

BACKGROUND

At present, demanding on gemstone identification is increasing, and as the rapid development of artificial-gemstone technology, the gemstone identification has become increasingly difficult. There are generally five detection methods for gemstone identification, including: 1) identification by macroscopic observation (for example, observing color, shape, luster, cleavage, etc.); 2) identification by physical property testing (for example, testing relative density, refractive index, hardness, etc.); 3) identification by polarizing microscope based on crystal optical properties; 4) chemical composition analysis (for example, simple chemical analysis, bulk chemical analysis, electron probe microanalysis, etc.); and 5) crystal structure analysis (for example, x-ray diffraction analysis, infrared spectroscopic analysis, electronic probe analysis, Raman spectrometer analysis, gemstone spectroscope analysis, ultraviolet spectrophotometer analysis, etc.). In the testing process of the methods 1), 2) and 3), the analysis results thereof rely heavily on experiences of operators and are affected greatly by subjective factor, and therefore, it is not conducive to form a standard for objectively measuring the authenticity of a gemstone. The method 4) has disadvantages of slow processing speed and often leading to damage the sample, and due to the specificity of gemstone that the gemstone cannot be cut, scratched, broken or eroded arbitrarily, the use of the chemical analysis is limited. In the prior art of gemstone identification, modern analytical instruments as used in the method 5) are more often used for identification, but the gemstone identification devices commonly used in the method 5) have a lot of disadvantages, such as expensive prices thereof, high analysis cost and slow analyzing speed, etc.

The ultraviolet spectrophotometer is most commonly used as a traditional crystal structure analysis instrument, but the ultraviolet spectrophotometer used in measurement is facing the following problems.

1. When an irregular shaped (often called baroque-shaped) gemstone is tested, a incident light may be reflected in any direction from the surface of the gemstone, while the sampling system of the traditional ultraviolet spectrophotometer has a fixed optical path so that it is difficult to ensure a high efficiency collection of reflected light for baroque-shaped samples, and therefore, there is uncertainty in the measurement of baroque-shaped samples.

2. All traditional ultraviolet spectrophotometers use pre splitting, that is, a composite light from a light source would become monochromatic lights after light splitting by a beam splitter and a monochromator, to irradiate to samples, and information would be recorded by an optoelectronic detector. In order to achieve a continuous record of photometric value at different wavelengths, it needs rotation and adjustment of a mechanical device. And it needs to extend the sweep time to ensure the wavelength resolution, resulting in low measurement efficiency. In addition, with the use of a precision mechanical rotating device, there are high demands for debugging and installation of the prior art of the measuring instrument, causing a complex process of the instrument and high cost. Such measurement method is not suitable to the current gemstone identification.

SUMMARY

In order to solve the above technical problem, the present disclosure provides a reflectance spectroscopy measuring and sampling method for gemstone testing, which can detect baroque-shaped samples conveniently and accurately at extremely high testing speed. The present disclosure also provides a reflectance spectroscopy measuring and sampling system for gemstone testing, which can detect baroque-shaped samples conveniently and accurately at extremely high testing speed.

The proposed technical solution according to the present disclosure to solve the above technical problem is as below.

A reflectance spectroscopy measuring and sampling system for gemstone testing, including: a first light source, a second light source, a light filtering element, an integrating sphere, an optical fiber, a spectroscopic detection module, an analog-digital conversion module, and a data processing terminal, wherein the integrating sphere is provided with an entrance port, a sampling opening and a reflected light exit port.

Lights from the first light source and the second light source are filtered by the light filtering element to get an ultraviolet-visible-near-infrared continuous polychromatic light which incidents into the interior of the integrating sphere through the entrance port of the integrating sphere, hits the sample through the sampling opening after multiple diffuse reflections in the integrating sphere, and then is reflected by the sample to form a reflected light; the reflected light and reflected lights formed by the diffuse reflections in the integrating sphere are introduced into the spectroscopic detection module via the optical fiber connected to the reflected light exit port; the reflected lights are splitted and then detected by the spectroscopic detection module, photonic information of the reflected lights are converted into electronic signals in accordance with the order of wavelengths thereof, the electronic signals are converted into digital signals via the analog-digital conversion module, and the digital signals are transferred to the data processing terminal to form a real-time spectrogram.

Preferably, the spectroscopic detection module can include an entrance slit, a collimating mirror, a grating, a second collecting mirror and a CCD sensitive array, the reflected light can be incident on the collimating mirror through the entrance slit and hit the grating after being collimated by the collimating mirror, then light splitted by the grating can reach the second collecting mirror to be focused to hit the CCD sensitive array.

Preferably, the system can also include a first optical lens group, the light filtering element can be a dichroscope, the entrance port can be a first entrance port, the sampling opening can be arranged on the top of the integrating sphere, and the first entrance port and the reflected light exit port can be dividually arranged on the side and bottom of the integrating sphere respectively.

Light from the first light source and the second light source can be filtered via the dichroscope, and pass through the first optical lens group and the first entrance port to be incident into the interior of the integrating sphere.

Preferably, the system can also include a second optical lens group and a third optical lens group, the light filtering element can include a first light filter and a second light filter, the entrance port can include a second entrance port and a third entrance port, the sampling opening can be arranged on the top of the integrating sphere, the reflected light exit port can be arranged on the bottom of the integrating sphere, and the second entrance port and the third entrance port can be arranged on two sides of the integrating sphere respectively.

Light from the first light source passes through the first light filter, the second optical lens group and the second entrance port to be incident into the interior of the integrating sphere, and light from the second light source passes through the second light filter, the third optical lens group and the third entrance port to be incident into the interior of the integrating sphere.

Preferably, a first collecting mirror can be arranged on the reflected light exit port and/or an optically clear quartz plate can be arranged on the sampling opening.

Another proposed technical solution according to the present disclosure to solve the above technical problem is as below.

A reflectance spectroscopy measuring and sampling method for gemstone testing includes:

step S1, filtering light from a first light source and a second light source to get an incident light, which is incident into the interior of an integrating sphere through an entrance port on the integrating sphere;

step S2, making the incident light hit the sample through a sampling opening after multiple diffuse reflections in the integrating sphere and be reflected on the sample, resulting in a reflected light;

step S3, sampling the reflected light and reflected lights formed by the diffuse reflections in the integrating sphere via a reflected light exit port, and introducing the reflected light into a spectroscopic detection module via an optical fiber.

step S4, splitting and then detecting the reflected lights with a spectroscopic detection module, which then converts photonic information of the reflected lights into electronic signals in accordance with the order of wavelengths; and step S5, converting the electronic signal into a digital signal via an analog-digital conversion module, and transferring the digital signal to a data processing terminal to form a real-time spectrogram.

Preferably, the step S4 includes:
making the reflected lights be incident on a collimating mirror through a entrance slit and hit a grating after being collimated by the collimating mirror, making the light splitted by the grating reach a second collecting mirror to be focused to hit the CCD sensitive array for detecting, and converting photonic information of the reflected lights into electronic signals in accordance with wavelength order.

Preferably, the step S1 includes:
filtering light from the first light source and the second light source via a dichroscope to get an ultraviolet-visible-near-infrared continuous polychromatic light as an incident light, and focusing the incident light via a first optical lens group to pass through a first entrance port to be incident into the interior of the integrating sphere.

Preferably, the step S1 includes:
filtering light from the first light source via a first light filter to get a first incident light, and focusing the first incident light via a second optical lens group to pass through a second entrance port to be incident into the interior of the integrating sphere; and filtering light from the second light source via a second light filter to get a second incident light, and focusing the second incident light via a third optical lens group to pass through a third entrance port to be incident into the interior of the integrating sphere.

Preferably, the step S3 includes:
sampling the reflected light and reflected lights formed by the diffuse reflections in the integrating sphere via a first collecting mirror arranged on the reflected light exit port, and introducing the reflected light into a spectroscopic detection module via an optical fiber.

The present disclosure has an advantage as below. The reflectance spectroscopy measuring and sampling system for gemstone testing according to the present disclosure filters light from a first light source and a second light source to be used as an incident light which can be incident into the interior of the integrating sphere and hit the sample directly in the diffuse reflection or by multiple diffuse reflection in the integrating sphere. Light reflected on the sample can be sampled and handled by the system to get a real-time spectrogram. The system according to the present disclosure can collect a real-time spectrogram of light reflected by the gemstone and obtain information of "full spectrum" from a range of wavelengths selected by a user, to solve the uncertainty problems arise from the baroque-shaped samples measurement, without same complex operations, such as monochrome scanning or mechanische spektroskopie, and it greatly promotes the efficiency of detection, analysis and test of the gemstone.

The present disclosure has another advantage as below. A reflectance spectroscopy measuring and sampling method for gemstone testing according to the present disclosure filters light from a first light source and a second light source to be used as an incident light which can be incident into the interior of the integrating sphere and hit the sample directly in the diffuse reflection or by multiple diffuse reflection within the diffuse reflection. Light reflected on the sample can be sampled and handled to get a real-time spectrogram. The method according to the present disclosure can collect a real-time spectrogram of light reflected by the gemstone and obtain information of "full spectrum" from a range of wavelengths selected by a user, to solve the uncertainty problems arise from the baroque-shaped samples measurement, without same complex operations, such as monochrome scanning or mechanische spektroskopie, and it greatly promotes the efficiency of detection, analysis and test of the gemstone.

BRIEF DESCRIPTION OF THE DRAWINGS

The present disclosure may be understood better by reference to the following description taken in conjunction with the accompanying drawings.

DETAILED DESCRIPTION OF THE PREFERRED EMBODIMENTS

With the desire for ease of description, the following terms are explained at first.

CCD: Charge-coupled Device, configured to convert optical signals into electronic signals.

Figure 1:
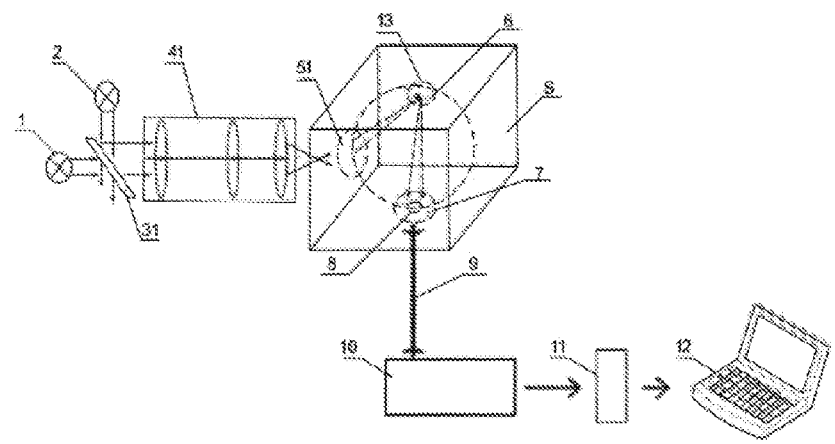
FIG. 1 is a structure diagram illustrating a reflectance spectroscopy measuring and sampling system for gemstone testing according to one embodiment of the present disclosure.

See FIG. 1, the present disclosure provides a reflectance spectroscopy measuring and sampling system for gemstone testing, including a first light source 1, a second light source 2, a light filtering element, an integrating sphere S, an optical fiber 9, a spectroscopic detection module 10, an analog-digital conversion module 11 and a data processing terminal 12, wherein the integrating sphere S is provided with an entrance port, a sampling opening 6 and a reflected light exit port 7.

Light from the first light source 1 and the second light source 2 is filtered by the light filtering element, be incident into the interior of the integrating sphere S through the entrance port on the integrating sphere S, hit the sample 13 through the sampling opening 6 after multiple diffuse reflections within the integrating sphere S, and be reflected on the sample 13, resulting in a reflected light. The reflected light and reflected lights formed by the diffuse reflections in the integrating sphere S are led into the spectroscopic detection module 10 via the optical fiber 9 connected to the reflected light exit port 7. The reflected light is splitted and detected by the spectroscopic detection module 10, photonic information of the reflected lights are converted into electronic signals in accordance of wavelengths thereof, and the electronic signals are converted to digital signals via the analog-digital conversion module 11, to be transferred to the data processing terminal 12 to form a real-time spectrogram.

Figure 3:
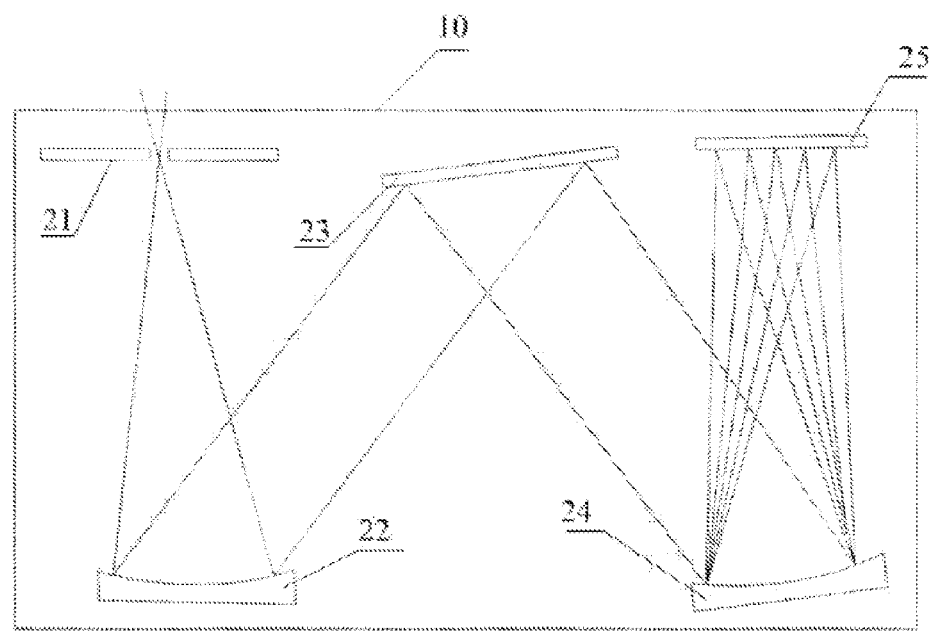
FIG. 3 is a structure diagram illustrating a spectroscopic detection module according to one embodiment of the present disclosure.

In a preferred embodiment, as shown in FIG. 3, the spectroscopic detection module 10 includes an entrance slit 21, a collimating mirror 22, a grating 23, a second collecting mirror 24 and a CCD sensitive array 25, the reflected light is incident on the collimating mirror 22 through the entrance slit 21 and hit the grating 23 after being collimated by the collimating mirror 22, then light splitted by the grating 23 reaches the second collecting mirror 24 to be focused to hit the CCD sensitive array 25. In the embodiment, the split light is focused by the second collecting mirror 24 to hit different positions of the CCD sensitive array 25, and the CDD in each position of the array detects the light which is incident on the CCD. The intensity of light at different wavelength in the split light is detected by a reasonable number and distribution of CDD in the CCD sensitive array. In one embodiment, the grating 23 is a plane grating.

Figure 2:
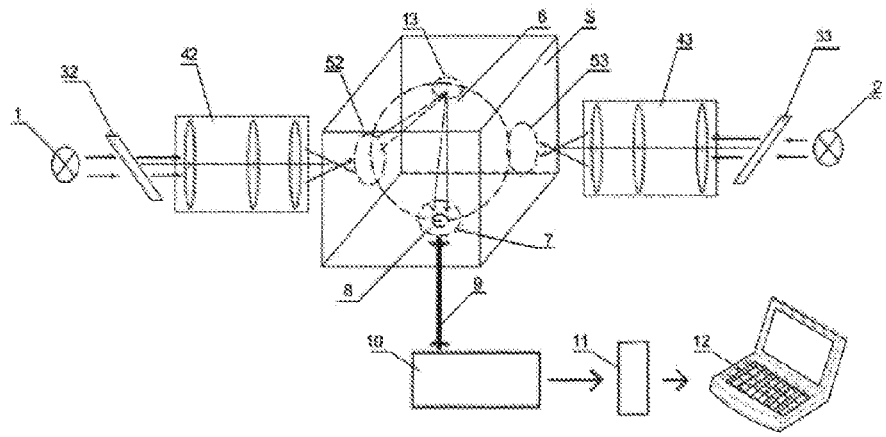
FIG. 2 is a structure diagram illustrating a reflectance spectroscopy measuring and sampling system for gemstone testing according to another embodiment of the present disclosure.

In a preferred embodiment, as shown in FIG. 2, the system further includes a first optical lens group 41, the light filtering element is a dichroscope 31, the entrance port is a first entrance port 51, the sampling opening 6 is arranged on the top of the integrating sphere S, and the first entrance port 51 and the reflected light exit port 7 is dividually arranged on the side and bottom of the integrating sphere S respectively.

Light from the first light source 1 and the second light source 3 is filtered via the dichroscope 31 to get an ultraviolet-visible-near-infrared continuous polychromatic light which passes through the first optical lens group 41 and the first entrance port 51 to be incident into the interior of the integrating sphere S.

Preferably, in the above embodiment, the first light source 1 is a deuterium lamp, the second light source 2 is a halogen tungsten lamp, and the dichroscope 31 is a dichroscope with a high transmittance for light with a wavelength under 400 nm, and with a high reflectance for a light with a wavelength above 400 nm. The deuterium lamp provides ultraviolet light with a wavelength under 400 nm and a light with a peak above 400 nm, and the halogen tungsten lamp provides visible light to near-infrared light with a wavelength at a range of 350 nm-2200 nm. The light having a peak with a wavelength above 400 nm from the deuterium lamp emits energy of magnitude larger than the light from the halogen tungsten lamp. Because the dichroscope 31 is a dichroscope with a high transmittance for light with a wavelength under 400 nm and with a high reflectance for a light with a wavelength above 400 nm, when light from the deuterium lamp and the halogen tungsten lamp passes through the dichroscope 31, the light with a wavelength above 400 nm from the deuterium lamp and the light with a wavelength under 400 nm from the halogen tungsten lamp is filtered selectively, to make the light from the two light sources balance to form a polychromatic light with a wavelength at a range of 200-2200 nm. Because the gemstone has an absorption characteristic for specific wavelength peak or waveband, the gemstone is distinguished by comparing the collected real-time spectrogram of light reflected by the gemstone with a standard spectrogram corresponding to the gemstone published in the industry.

In a preferred embodiment, as shown in FIG. 3, the system also includes a second optical lens group 42 and a third optical lens group 43, the light filtering element includes a first light filter 32 and a second light filter 33, the entrance port includes a second entrance port 52 and a third entrance port 53, the sampling opening 6 is arranged on the top of the integrating sphere S, the reflected light exit port 7 is arranged on the bottom of the integrating sphere S, and the second entrance port 52 and the third entrance port 53 are arranged on two sides of the integrating sphere respectively S. Light from the first light source 1 passes through the first light filter 32, the second optical lens group 42 and the second entrance port 52 to be incident into the interior of the integrating sphere S, and light from the second light source 2 passes through the second light filter 33, the third optical lens group 43 and the third entrance port 53 to be incident into the interior of the integrating sphere S.

Preferably, in the above embodiment, the first light source 1 is a deuterium lamp, and the second light source 2 is a halogen tungsten lamp. In the embodiment, the role of the first light filter 32 and a second light filter 33 is the same as that of the dichroscope 31 that the light with a wavelength above 400 nm from the deuterium lamp is filtered by the first light filter 32, and the light with a wavelength under 400 nm from the halogen tungsten lamp is filtered by the second light filter 33, and the two light beams eventually entering into the integrating sphere S have wavelengths covering 200-2200 nm band and balanced energy. In the embodiment, the dichroscope 31 is replaced by two filters, and two light beams from the two light sources are focused via two optical lens groups respectively and incident into the interior of the integrating sphere S from two sides of the integrating sphere S.

In a preferred embodiment, a first collecting mirror 8 is arranged on the reflected light exit port 7 and/or an optically clear quartz plate is arranged on the sampling opening 6. When installing the first collecting mirror 8, a beam of light is incident to the reflected light exit port 7, if the first collecting mirror 8 is placed in a position to make the beam of light be focused on the sampling opening 6, the position is a proper position for the first collecting mirror 8. According to reversibility of optical path, the reflected light from the sampling opening is collected by the first collecting mirror 8. In the embodiment, the first collecting mirror 8 better collects reflected light and reflected lights formed by the diffuse reflections in the integrating sphere S, to achieve the greatest benefit of collection. With the first collecting mirror 8 arranged on the reflected light exit port 7, samples are directly placed on the quartz plate that the sample in any shape is tested.

Figure 4:
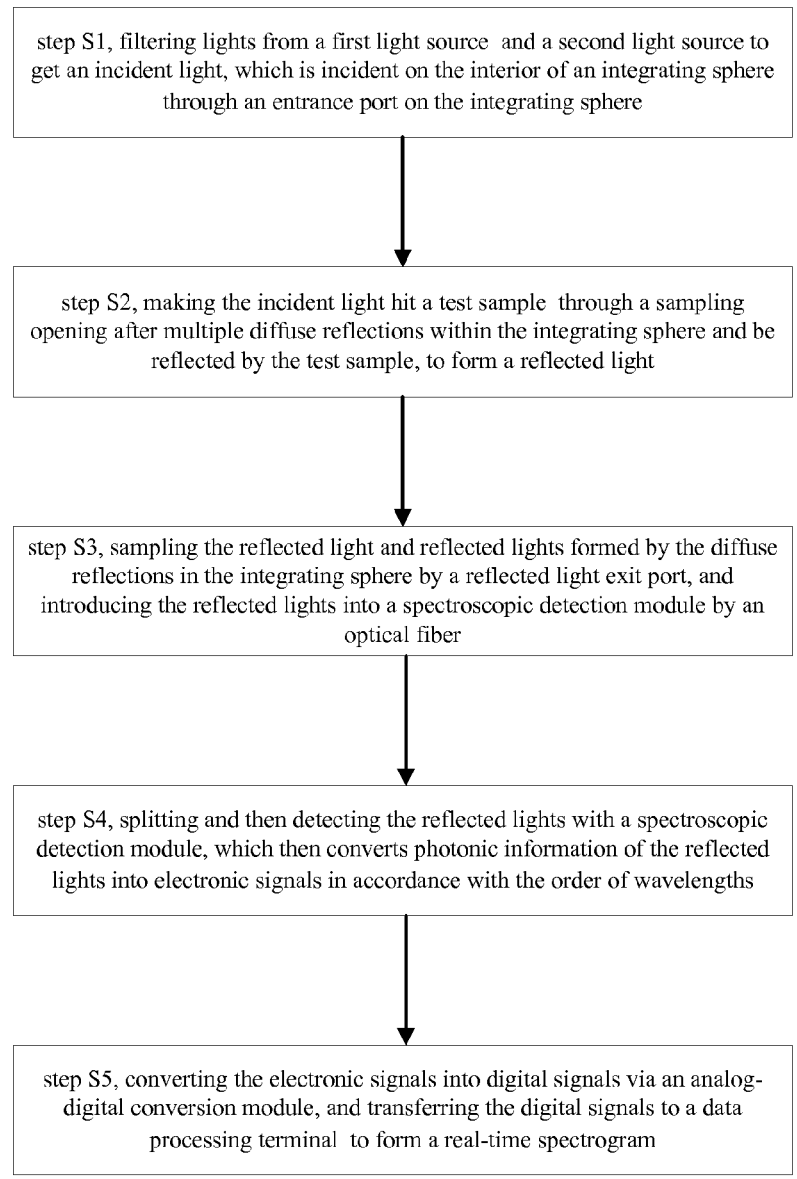
FIG. 4 is a flow diagram illustrating a reflectance spectroscopy measuring and sampling method for gemstone testing according to one embodiment of the present disclosure.

See FIG. 4, the present disclosure also provides a reflectance spectroscopy measuring and sampling method for gemstone testing, including:

step S1, filtering light from a first light source 1 and a second light source 2 to get an incident light, which is incident into the interior of an integrating sphere through an entrance port on the integrating sphere S;

step S2, making the incident light hit the sample 13 through a sampling opening 6 after multiple diffuse reflections within the integrating sphere S and be reflected on the sample 13, resulting in a reflected light;

step S3, sampling the reflected light and reflected lights formed by the diffuse reflections in the integrating sphere S via a reflected light exit port 7, and introducing the reflected light into a spectroscopic detection module 10 via an optical fiber 9.

step S4, splitting and then detecting the reflected lights with a spectroscopic detection module 10, which then converts photonic information of the reflected lights into electronic signals in accordance with the order of wavelengths; and step S5, converting the electronic signal into a digital signal via an analog-digital conversion module 11, and transferring the digital signal to a data processing terminal 12 to form a real-time spectrogram.

After getting a reflection spectrogram of ultraviolet light, visible light or near-infrared light, and part of infrared light, the gemstone samples are identified scientifically, accurately and quickly. The gemstone herein includes all kinds of jewelry, such as diamond, golden pearl, red coral or emerald.

Figure 5:
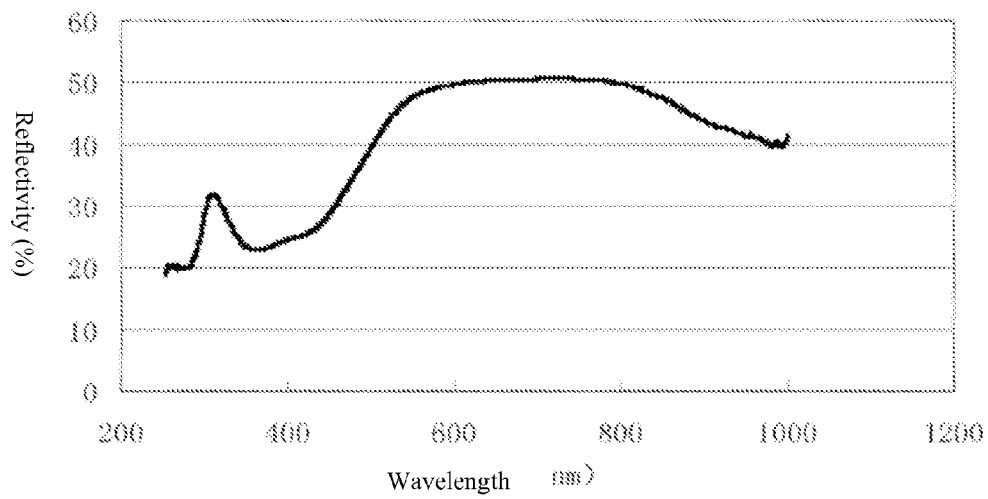
FIG. 5 is a real-time spectrogram from a test on a natural golden pearl based on the method according to one embodiment of the present disclosure.

FIG. 5 is a real-time spectrogram obtained from a test on a natural golden pearl based on the method according to one embodiment of the present disclosure. Based on the identification standards published the jewelry industry that the natural golden pearl has a characteristic absorption peak between 360 nm and 420 nm for light, the natural golden pearl is identified by the spectrogram from tests.

Figure 6:
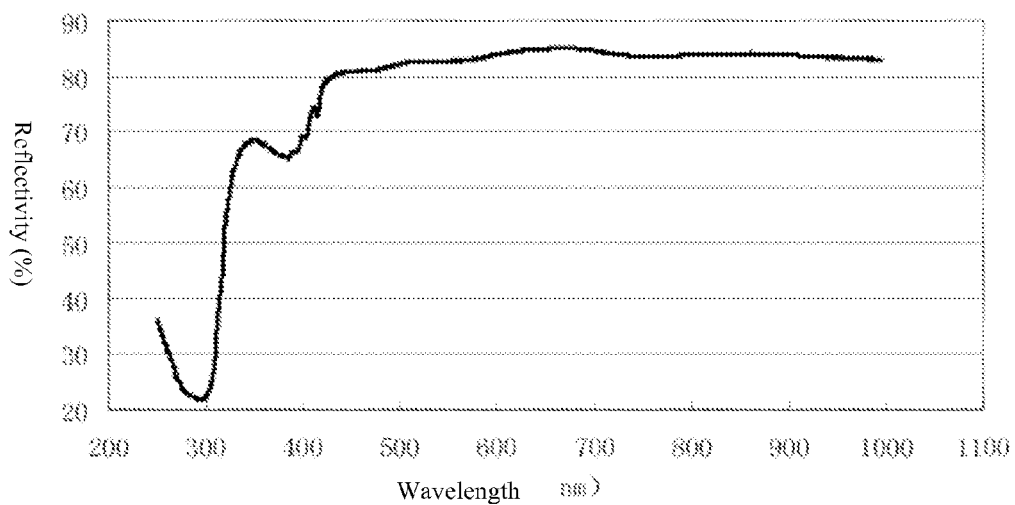
FIG. 6 is a real-time spectrogram from a test on a natural diamond based on the method according to one embodiment of the present disclosure.

FIG. 6 is a real-time spectrogram obtained from a test on a natural diamond based on the method according to one embodiment of the present disclosure. Based on the identification standards published the jewelry industry that the natural diamond has a characteristic absorption peak between 300 nm and 415 nm for light, the natural diamond is identified by the spectrogram from tests.

In a preferred embodiment, the step S4 includes:

making the reflected light be incident on a collimating mirror 22 through a entrance slit 21 and hit a grating 23 after being collimated by the collimating mirror 22, making the light splitted by the grating 23 reach a second collecting mirror 24 to be focused to hit the CCD sensitive array 25 for detecting, and converting photonic information of the reflected light into an electronic signal in order of wavelength.

In a preferred embodiment, the step S1 includes:

filtering light from the first light source 1 and the second light source 2 via a dichroscope 31 to get an ultraviolet-visible-near-infrared continuous polychromatic light as an incident light, and focusing the incident light via a first optical lens group 41 to pass through a first entrance port 51 to be incident into the interior of the integrating sphere S.

In a preferred embodiment, the step S1 includes:

filtering light from the first light source 1 via a first light filter 32 to get a first incident light, and focusing the first incident light via a second optical lens group 42 to pass through a second entrance port 52 to be incident into the interior of the integrating sphere S; and filtering light from the second light source 2 via a second light filter 33 to get a second incident light, and focusing the second incident light via a third optical lens group 43 to pass through a third entrance port 53 to be incident into the interior of the integrating sphere S.

In a preferred embodiment, the step S3 includes:

sampling the reflected light and reflected lights formed by the diffuse reflections in the integrating sphere S via a first collecting mirror 8 arranged on the reflected light exit port 7, and introducing the reflected light into a spectroscopic detection module 10 via an optical fiber 9. In the embodiment, the first collecting mirror 8 collects the reflected light from the sample and the reflected lights formed by the diffuse reflections in the integrating sphere S at an angle of 8° achieves the greatest benefit of collection.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A reflectance spectroscopy measuring and sampling system for a gemstone sample, comprising:
    a deuterium lamp adapted to provide an ultraviolet light having a wavelength less than 400 nm, and a halogen lamp adapted to provide a visible-to-near-infrared light having a wavelength in a range of 350 nm-2200 nm;
    an integrating sphere having a side, a top, and a bottom, and interior and outer peripheries,
    an entrance port disposed on the side, a sampling opening disposed on the top, and a reflected light exit port disposed on the outer periphery on the bottom,
    a first collecting mirror disposed on the reflected light exit port and/or an optically clear quartz plate disposed on the sampling opening;
    a dichroscope adapted to selectively filter the light emitted from the deuterium lamp that has a light wavelength greater than 400 nm and the light emitted from the halogen lamp that has a light wavelength less than 400 nm to create an ultraviolet-visible-near-infrared continuous polychromatic light;

an optical lens adapted to focus the polychromatic light, wherein the polychromatic light passes through the entrance port into the interior and contacts the gemstone sample though the sampling opening after the polychromatic light undergoes multiple diffuse reflections in the integrating sphere, and the polychromatic light is then reflected by the gemstone sample after contact to form a reflected light;

an optical fiber operably coupled to the reflected light exit port and adapted to receive and convey the reflected light into a spectroscopic detection module that is adapted to split the reflected light and convert photonic information contained in the reflected light into analog signals according to an order of wavelengths of the reflected light, wherein the spectroscopic detection module includes an entrance slit, a collimating mirror adapted to collimate light, a grating adapted to split light, a second collecting mirror, and a CCD sensitive array, wherein the reflected light is incident and collimated on the collimating mirror through the entrance slit and is then transferred to the grating and is split, and then is transferred to the second collecting mirror to be focused on the CCD sensitive array;

an analog-digital conversion module operably coupled to the spectroscopic detection module and adapted to respectively convert the analog signals into digital signals; and a data processing terminal adapted to receive the digital signals and form a real-time spectrogram based on the digital signals.

2. A reflectance spectroscopy measuring and sampling system for a sample, comprising:

a deuterium lamp adapted to emit an ultraviolet light having a wavelength less than 400 nm and a halogen lamp adapted to emit a visible-to-near-infrared light having a wavelength in a range of 350 nm-2200 nm;

an integrating sphere including interior and outer peripheries, first and second sides, a top, and a bottom, first and second entrance ports respectively disposed on the first and second sides, a sampling opening disposed on the top, and a reflected light exit port disposed on the outer periphery on the bottom, a first collecting mirror disposed on the reflected light exit port and/or an optically clear quartz plate disposed on the sampling opening;

a first light filtering element adapted to filter light emitted from the deuterium lamp having a wavelength greater than 400 nm and pass-through the ultraviolet light;

a second light filtering element adapted to filter light emitted from the halogen lamp having a wavelength less than 400 nm and pass-through the visible-to-near-infrared light;

first and second optical lens respectively adapted to focus light filtered by the first and second light filtering elements, wherein light focused by the first and second optical lens respectively pass through the first and second entrance ports into the interior of the integrating sphere to form an ultraviolet-visible-near-infrared continuous polychromatic light that contacts the sample though the sampling opening after the polychromatic light undergoes multiple diffuse reflections in the integrating sphere, and the polychromatic light is reflected by the sample after contact to form a reflected light;

an optical fiber operably coupled to the reflected light exit port and adapted to receive and convey the reflected light into a spectroscopic detection module that is adapted to split the reflected light and convert photonic information contained in the reflected light into analog signals according to an order of wavelengths of the reflected light, wherein the spectroscopic detection module includes an entrance slit, a collimating mirror adapted to collimate light, a grating adapted to split light, a second collecting mirror, and a CCD sensitive array, and wherein the reflected light is incident and collimated on the collimating mirror through the entrance slit and is then transferred to the grating and is split, and is then transferred to the second collecting mirror to be focused on the CCD sensitive array;

an analog-digital conversion module operably coupled to the spectroscopic detection module and adapted to respectively convert the analog signals into digital signals; and a data processing terminal adapted to receive the digital signals and form a real-time spectrogram based on the digital signals.

* * * * *